United States Patent [19]

Dahl et al.

[11] Patent Number: 4,969,463
[45] Date of Patent: Nov. 13, 1990

[54] DEFIBRILLATION ELECTRODE AND METHOD FOR EMPLOYING GATLING DISCHARGE DEFIBRILLATION

[75] Inventors: Roger W. Dahl, Andover; Stanley M. Bach, Jr., Shoreview; Ronald W. Heil, Jr., Rosevill, all of Minn.; Mieczyslaw Mirowski, Owings Mills, Md.

[73] Assignee: Cardiac Pacemakers, Inc., St. Paul, Minn.

[21] Appl. No.: 361,978

[22] Filed: Jun. 6, 1989

[51] Int. Cl.[5] .................................................. A61N 1/00
[52] U.S. Cl. .............................. 128/419 D; 128/419 P
[58] Field of Search .......... 128/419 P, 419 D, 419 PG

[56] References Cited

U.S. PATENT DOCUMENTS

| | | | |
|---|---|---|---|
| 3,937,226 | 2/1976 | Funke | 128/419 D |
| 4,548,203 | 10/1985 | Tacker, Jr. et al. | 128/419 D |
| 4,603,705 | 8/1986 | Speicher et al. | 128/419 D |
| 4,637,397 | 1/1987 | Jones et al. | 128/419 D |
| 4,641,656 | 2/1987 | Smits | 128/491 D |
| 4,708,145 | 11/1987 | Tracker, Jr. et al. | 128/419 D |
| 4,768,512 | 9/1988 | Imran | 128/419 D |
| 4,774,952 | 10/1988 | Smits | 128/419 D |
| 4,800,883 | 1/1989 | Winstrom | 128/419 D |
| 4,827,932 | 5/1989 | Ideker et al. | 128/419 |
| 4,834,100 | 5/1989 | Charms | 128/419 P |

Primary Examiner—Francis Jaworski
Assistant Examiner—George Mauuel
Attorney, Agent, or Firm—Fleit, Jacobson, Cohn, Price, Holman & Stern

[57] ABSTRACT

An implantable defibrillation/cardioversion system and method comprising an electrode having a plurality of discrete electrically conductive segments. The conductive segments are electrically isolated from each other and electrically connected to a defibrillation/cardioversion unit. An electrical pulse block is generated and chopped into a plurality of discrete pulse segments by the defibrillation/cardioversion unit and applied to the electrode so that each conductive segment receives a particular electrical pulse assigned from the series of pulses. In this way, the concentration of gas generated from ionic current produced by a high energy defibrillation pulse is reduces and more energy is delivered to the heart, thus reducing the required energy input to the electrode. The electrode may be planar or in a catheter electrode configuration.

41 Claims, 5 Drawing Sheets

DEFIBRILLATION ELECTRODE AND METHOD FOR EMPLOYING GATLING DISCHARGE DEFIBRILLATION

BACKGROUND OF THE INVENTION

This invention relates to an electrode and a method for stimulating tissue in medical applications, and more particularly to an implantable cardiac defibrillation electrode together with associated electronics and a method for performing cardiac defibrillation.

Electrodes implanted in the body for electrical stimulation are well known. More specifically, electrodes implanted on or about the heart have been used to reverse (i.e., defibrillate or cardiovert) certain life-threatening cardiac arrhythmias, by applying electrical energy to the heart via these electrodes to return the heart to normal sinus rhythm. The amount of energy delivered to the heart during defibrillation (or cardioversion) depends on the placement of the electrodes on or about the heart and the ability of the electrodes to distribute the energy uniformly through the heart.

Prior devices for efficiently delivering defibrillation waveforms from electrodes to heart tissue also are known. See for example, commonly assigned U.S. Pat. No. 4,768,512. In this prior device, a truncated exponential defibrillation pulse is chopped into a plurality of consecutive pulse segments and delivered to the heart via an electrode pair. Such high frequency waveforms compensate for the various frequency-dependent impedances throughout the heart tissue to distribute energy more effectively.

The present invention is based upon the recognition that the high energy delivered to a fibrillating heart during defibrillation causes at ionic current to develop at the electrodes. The conversion from an electric current to an ionic current produces gas at the electrode-tissue interface which acts as an insulator between the electrode and the tissue to which the defibrillating energy is being delivered. As a result, the amount of electrical energy actually delivered to the tissue from the electrode is reduced, and therefore, some of the defibrillating electric field developed between the electrodes never effectively reaches the heart. Accordingly, there is a need to increase the ability of defibrillation electrodes to deliver energy to a fibrillating heart.

By increasing the efficiency of the transfer of energy from the electrodes to the heart, the amount of energy required at as can be reduced. As a result, the size the input of the electrodes can be reduced. As a result, the size of the unit containing the defibrillation/cardioversion circuitry can be reduced, or the life of the unit can be correspondingly increased.

SUMMARY OF THE INVENTION

It is a primary object of this invention to meet the above requirements by providing a defibrillation electrode, a discharge circuit and a pulse discharge technique which reduces the concentration of gas produced by electrolysis at the electrode-tissue interface, thus increasing the efficiency of the energy transfer between implanted electrodes and the heart tissue receiving a defibrillating pulse.

It is a further object of this invention to increase the amount of energy transferred from the defibrillation electrode to the heart, and thus lower the required input energy to the electrode.

It is yet a further object of this invention to provide a defibrillation electrode and technique which reduces the required input energy to the electrodes and therefore either reduces the size or increases the life of the implanted unit containing the defibrillation electronic circuitry.

It is a further object of the present invention to provide a defibrillation electrode and technique for altering the shock vector about the heart for involving new muscle masses of the heart in the defibrillation episode.

In one embodiment, the defibrillation electrode discharge system of the present invention comprises an electrode having a plurality of separate, discrete conductive surfaces, each of which receives assigned pulses or time samples of a defibrillating waveform. The pulses are taken in succession until the waveform is exhausted, thus creating a "gatling" discharge. Time intervals are provided between successive pulses on any given segment to allow for the natural decay of the gas generated by electrolysis at the electrode-tissue interface. Therefore, the amount of gas present at the electrode-tissue interface is minimized. The interface impedance is thereby lowered, thus increasing the amount of energy delivered from the electrode to the tissue.

BRIEF DESCRIPTION OF THE DRAWINGS

FIG. 1b is a pictorial representation showing the relationship between time and the concentration of gas generated by ionic current resulting from the defibrillation pulse shown in FIG. 1a.

FIG. 5a is a plot of a single defibrillation pulse partitioned into discrete pulse segments in accordance with the teachings of the present invention.

FIG. 5b is a plot of the concentration of gas generated by electrolysis during the defibrillation pulse shown in FIG. 5a.

FIG. 9 is a plan view of a defibrillation electrode having separate alternating conductive wires wound around a catheter for use with the defibrillating pulsing technique illustrated in FIG. 5a.

DETAILED DESCRIPTION OF THE DRAWINGS

Figure 1A:
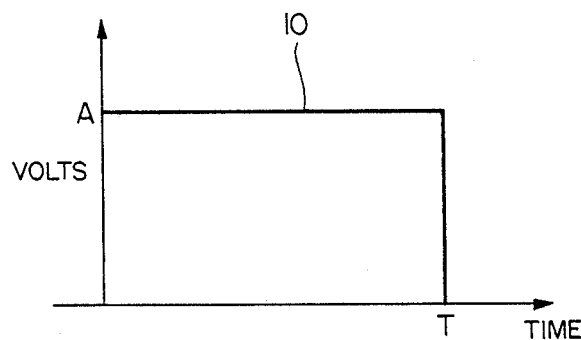
FIG. 1a is a pictorial representation of the voltage-time relationship of a defibrillation pulse.
Figure 1B:
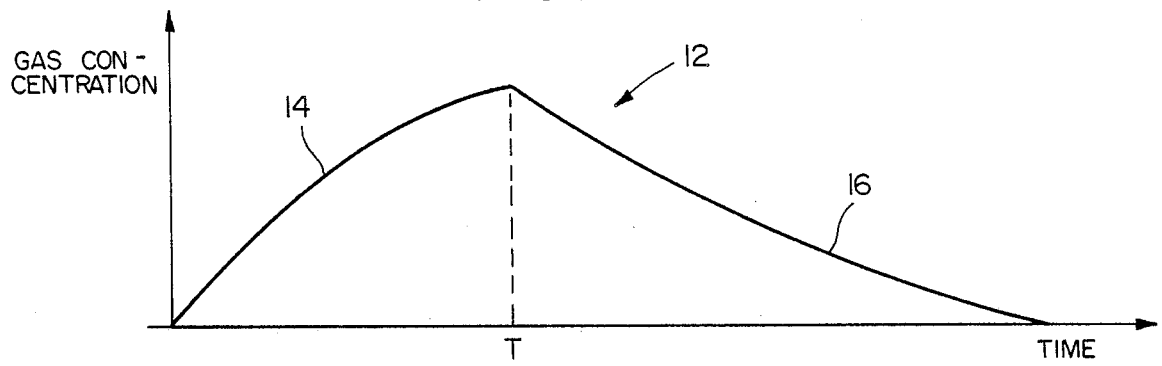

Referring first to FIG. 1a, a defibrillation pulse 10 is schematically shown having an amplitude A and a pulse width T. (Although the pulse 10 is depicted as a constant amplitude pulse, such a shape is for illustrative purposes only; the pulse 10 may be, for example an exponentially decaying, a bi-phasic, etc., waveform). Due to the high energy contained within the defibrillating pulse 10, ionic currents are generated at the electrode-tissue interfaces which cause the formation of gas between the defibrillation electrodes and the adjacent tissue. An illustrative plot of the gas formed due to the discharge of defibrillation pulse 10 is shown in FIG. 1b. As illustrated, the gas concentration increases exponentially during the discharge of the high energy defibrillation pulse. At the termination of the pulse, time T, the gas concentration decays exponentially to zero. It is known that the concentration of gas between the electrode and the adjacent tissue acts as an insulator which lowers the efficiency with which energy from a defibrillation electrode is delivered to the heart.

Figure 2:
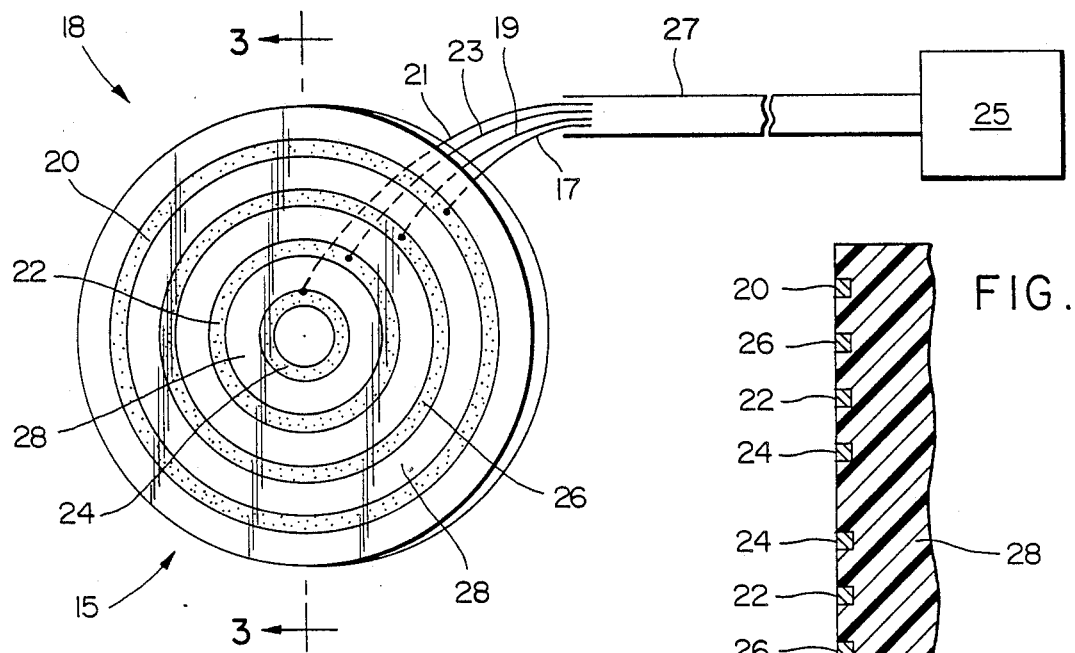
FIG. 2 is a perspective view of a defibrillation electrode having plural electrically conductive surfaces insulated from each other, in accordance with one embodiment of the present invention.
Figure 3:
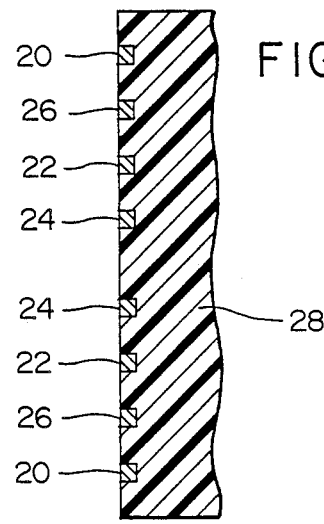
FIG. 3 is a cross-sectional view taken through line 3–3 of FIG. 2.

Referring now to FIGS. 2 and 3, a defibrillation electrode 18 is shown in accordance with one embodiment of the present invention. Electrode 18 comprises an active discharge surface region 15 comprised of discrete electrically conductive segments 20, 22, 24, and 26 in the form of spaced concentric rings. Each conductive segment is electrically isolated from the other conductive segment by insulator 28. Insulator 28 also isolates the conductive surfaces at their peripheral outer edges as well as their back surfaces.

The electrically conductive segments 20, 22, 24, and 26 are made, for example, of platinum iridium screen. Insulator 28 consists of silicon rubber sheets reinforced with woven dacron. The sheets, with such configuration, are laminated about the conductive segments to electrically isolate and support the conductive segments.

The conductive segments 20, 22, 24, and 26 are electrically connected to an implanted defibrillator/cardioverter unit 25 via insulated lead 27 of silicon rubber. (Only a single electrode 18 is shown; at least two electrodes are placed on or about the heart, as is well known in the art.) The lead 27 contains conductors 17, 19, 21, and 23, which connect conductive segments 20, 22, 24, and 26, respectively, to unit 25. The conductors 17, 19, 21, and 23 are, for example, Drawn Brased Strands (DBS) of silver and stainless steel. These conductors are electrically insulated and connect only their respective conductive segment to the defibrillator/cardioverter unit 25.

Figure 4:
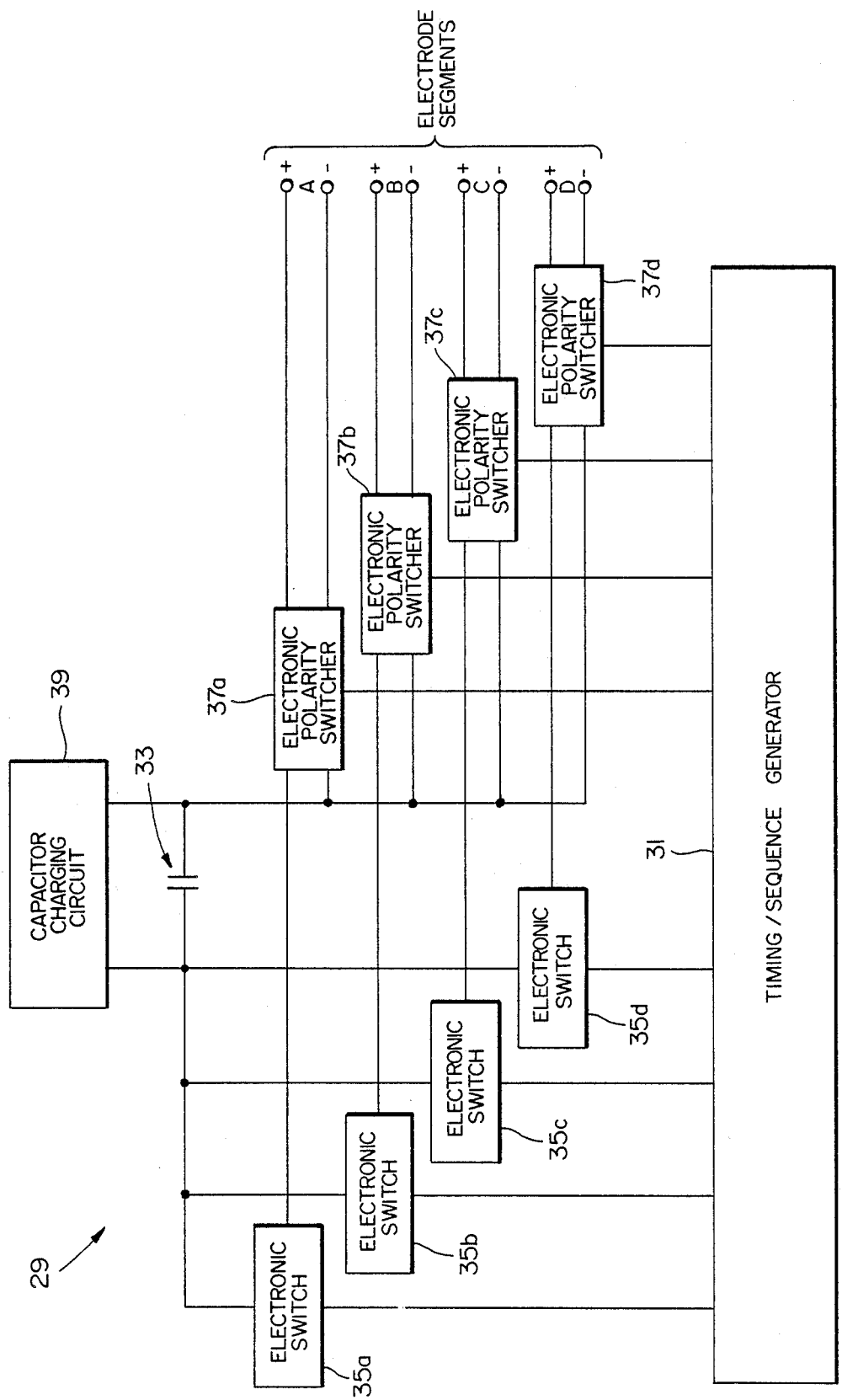
FIG. 4 is a schematic block diagram of the electronic circuit for performing the gatling discharge technique in accordance with the present invention.

Referring to FIG. 4, the discharge circuitry 29 of the defibrillator 25 is schematically illustrated. The discharge circuitry 29 comprises a timing/sequence generator 31 for controlling the discharge of capacitor 33 via electronic switches 35a–d and electronic polarity switches 37a–d. The capacitor 33 is charged by a charging circuit 39. The output terminals, labeled A, B, C, and D, are connected to the discrete electrode segments of electrode 18 via conductors 17, 19, 21, and 23.

The circuit 29 divides the defibrillation voltage shock stored by capacitor 33 into a series of pulses so that each pulse may be directed to or inhibited from any one or a combination of preselected electrode segments. The timing/sequence generator triggers the switches 35a–d to convey a predetermined portion of the voltage shock to the corresponding electrode segment. In addition, the polarity of the conveyed voltage shock portion can be altered by triggering the appropriate one of polarity switches 37a–d. While not shown, an arrhythmia detector is typically included within the pulse generator 25.

In operation, electrode 18 is implanted on or about the heart in conjunction with at least one other opposing electrode of the same or different construction. Connection to the pulse generator 25 is made, so that, for example, conductive segment 20 receives pulse segment A, conductive segment 22 receives pulse segment B, conductive segment 24 receives pulse segment C, and conductive segment 26 receives pulse segment D. This gatling discharge continues sequentially until the entire envelope, or pulse block 30 of the discharge pulse has reached the electrodes. The duty cycle, or pulse duration, however, may vary throughout the sequence allowing programmability for specific waveforms by storing data for controlling the timing/sequence generator 31. Further, as illustrated in phantom at C,, any pulse segment can be reversed in polarity.

Figure 5:
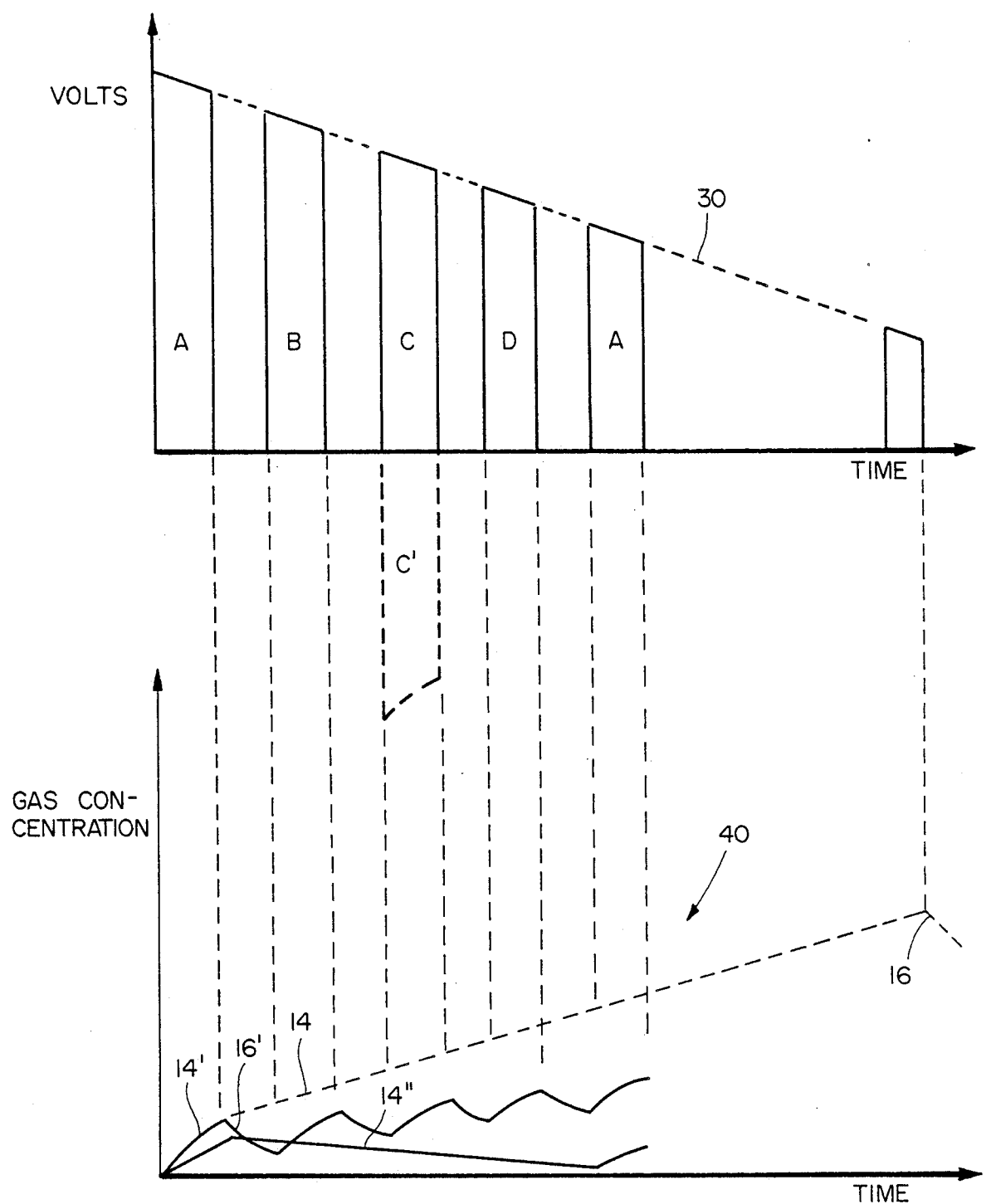

Moreover, by introducing a duty cycle, the amount of energy consumption is reduced. Referring to FIG. 5A, during the off periods between pulse segments, no energy is expended. As such, the height of the leading edge of a preceding pulse segment equals the height of the trailing edge of a subsequent pulse segment. Consequently, by lowering the duty cycle of pulsed shocks, the trailing edge voltage increases as well as the amount of energy remaining in the capacitor 33. This may allow for either a reduction in capacitor size, or a lowering of the leading edge voltages. Either approach reduces energy consumption without degrading efficiency.

Four conductive surface segments have been shown for illustrative purposes. However, more or less surface segments can be utilized to define the electrode, without departing from the spirit of the invention. The number of conductors of lead 27 and the number of defibrillator/cardioverter terminals would also change accordingly.

By having each conductive segment with its own conductor, all or only a portion of the conductive segments can be activated with the needs of the electrode. Further, by having only a portion of the segments activated at one time, the spatial distribution of the defibrillation energy can be optimized.

As a result of this gatling discharge technique, the formation of gas at the electrode-tissue interface is reduced as shown by plot 40 in FIG. 5b. Because the formation of gas is a product of the charge delivered by a pulse of high energy applied to the electrode, the reduction of time that this high energy pulse is present results both in a reduction in the amount of gas produced, and in the decay, or absorption, of the gas already produced.

For example, as seen in FIGS. 2, 5a, and 5b, the first conductive surface to receive energy is segment 20 (receiving pulse segment 32). During the presence of pulse segment A, gas will begin to form at the electrode-tissue interface of the entire electrode 18 as shown by curve portion 14'. However, at the termination of pulse segment A, the gas concentration begins to decay exponentially as described above in conjunction with FIG. 1b as shown in FIG. 5b by curve portion 16'. It is important to note that the formation of gas due to pulse segment A occurs primarily around the periphery of conductive segment 20. Further, the concentration of gas surrounding any particular conductive segment is illustrated by curve 14''. The gas concentration around a particular segment reaches a peak then decays until that particular segment receives another voltage shock. The accumulated gas formed from each electrode surface, and hence at the overall electrode, does not reach as high a level as would have been reached by a single pulse discharge at a single conductive surface.

As noted above, the overall effect of applying the pulsing technique shown in FIG. 5a to defibrillation electrode 18 results in a reduction in the accumulation of gas produced at the electrode-tissue interface. In this regard, it should be noted that the representation of FIG. 5b is an average, in that each of the four conductive segments receives one discharge pulse segment out of every four pulse segments delivered. Therefore, by reducing the presence of insulating gas, the efficiency with which energy is delivered from electrode 18 to the heart tissue is increased overall. The total amount of gas formed is a function of the amount of charge delivered. By reducing gas accumulation, the amount of surface remasking is reduced and the interface impedance is lowered.

The gatling discharge technique described above effectively defibrillates the heart by altering the shock vector applied to the heart. By changing the orientation of the shock vector, new muscle masses are involved. However, the voltage gradients of the same muscle mass is not affected by the changing shock vector.

Figure 6:
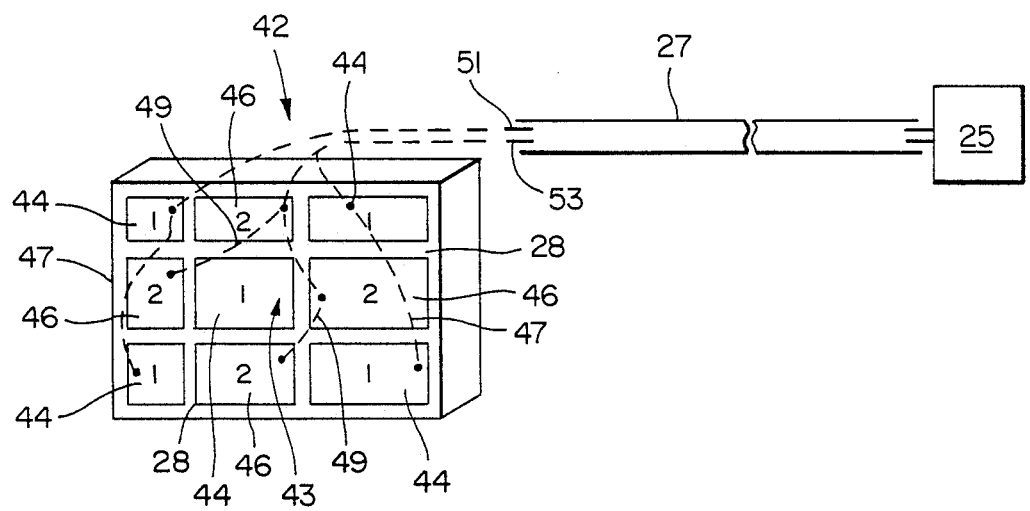
FIG. 6 illustrates a defibrillation electrode having an array of conductive surfaces connected so as to define two segmented discharge surfaces on the electrode.
Figure 7:
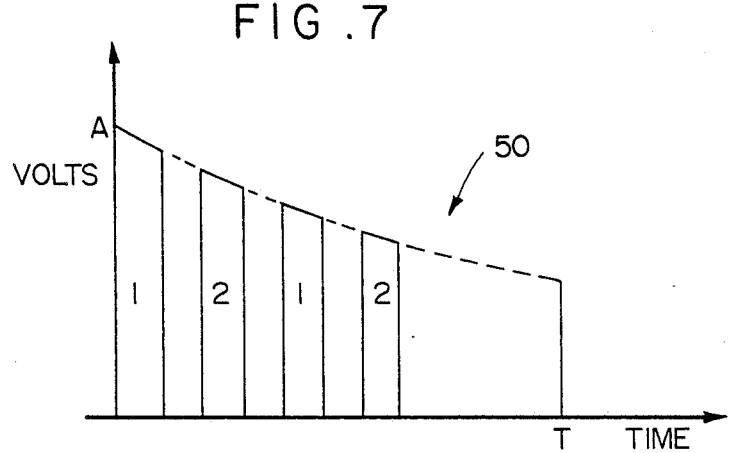
FIG. 7 shows the voltage-time relationship of a segmented pulsing technique applied to the electrode illustrated in FIG. 6.

FIGS. 6 and 7 illustrate another embodiment of the present invention. Defibrillation electrode 42 is provided with an active discharge surface region 43 comprised of conductive segments 44 and 46, formed of conductive mesh screens, of generally equal size and shape. The conductive segments 44 and 46 are insulated from one another by insulator 28, and are electrically connected together in two groups. Typically, electrode 42 has a cross section similar to that of electrode 18 shown in FIG. 3, with insulator 28 covering the entire rear and perimeter surfaces of the electrode. Conductors 47 and 49 connect together conductive segments 44 and 46, respectively. Conductors 51 and 53 are provided to connect the two groups of conductive segments to the defibrillator unit 25, similar to the connections illustrated in FIG. 2.

In operation, a pulse block 50, as shown in FIG. 7, similar to pulse block 30 of FIG. 5a is applied by defibrillator unit 25 to electrode 42. Two groups of conductive segments, labeled "1" and "2" for illustrative purposes and corresponding to conductive surfaces 44 and 46, are positioned throughout electrode 42 and receive pulses 52 and 54, respectively. As a result, the overall effect of reducing the amount of gas formed at the electrode-tissue interface is achieved as illustrated in FIG. 5b and previously described. The number of distinct conductive segments in a group, as well as the number of groups of conductive surfaces on electrode 42, can be increased for effecting specific discharge shapes and distributions.

Figure 8:
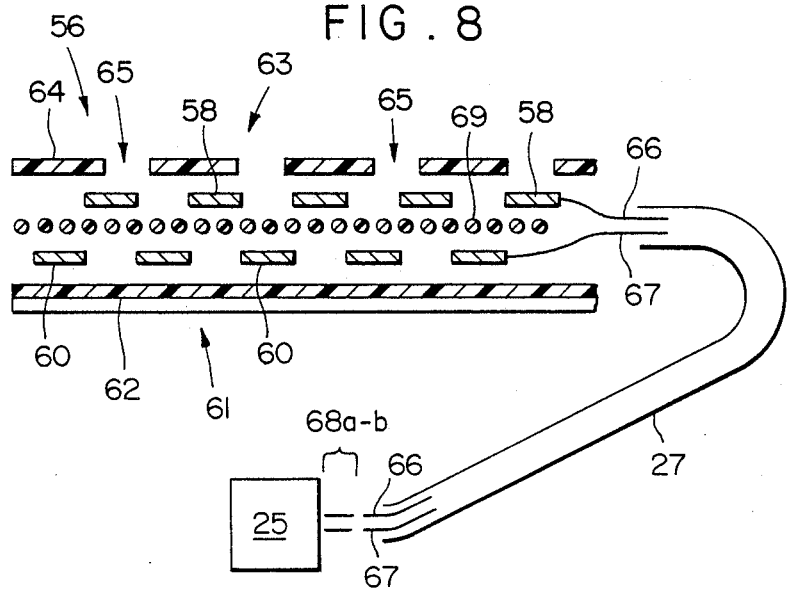
FIG. 8 is a cross-sectional view showing a defibrillation electrode of another embodiment, in unassembled form, having stacked electrically conductive mesh screens.

FIG. 8 illustrates still another embodiment of the present invention comprising defibrillation electrode 56 having a similar construction to electrode 18 shown in FIGS. 1 and 2 but differing in a few details. Specifically, defibrillation electrode 56 is provided with stacked electrically conductive mesh screens 58 and 60. Insulation 62 provides a non-conductive backing for non-active surfaces of electrode 56. A mask 64 is provided with apertures 65 exposing the electrically conductive screens 58 and 60 on the active discharge surface 63 of electrode 56. A dacron mesh or other porous insulator 69 is provided between screens 58 and 60. Conductors 66 and 67 connect screens 58 and 60 to the defibrillator unit 25. Mask 64 and insulation 62 are laminated together, enclosing screens 58 and 60.

In use, electrode 56 receives a pulse block similar to that illustrated in FIG. 7. Screens 58 and 60 are energized alternately, so that as described above, the gas generated about the heart surface is reduced, lowering the required energy for effecting defibrillation or cardioversion. Furthermore, while only two conductive screens are shown, additional screens can be used, each receiving an assigned discrete pulse segment.

Figure 9:
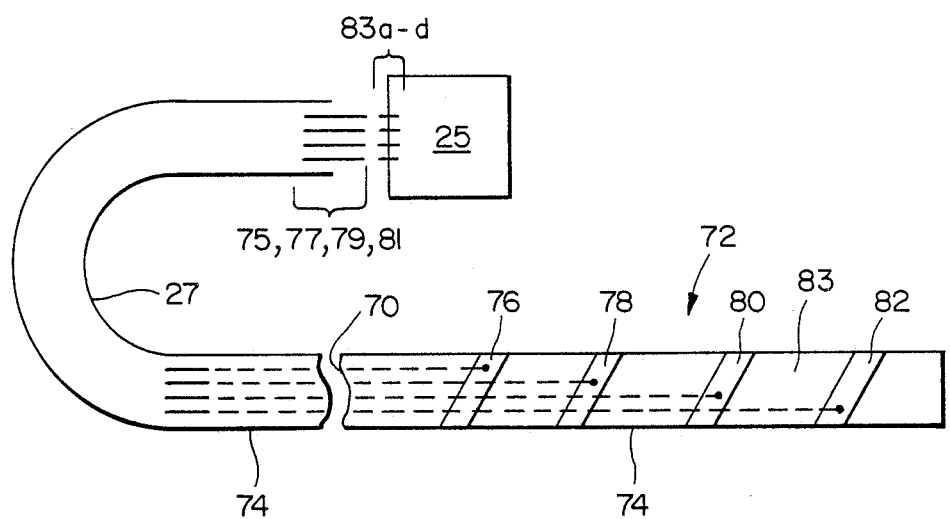

FIG. 9 illustrates a defibrillation electrode of yet another embodiment of this invention. Electrode 72 comprises a cardiac catheter 74 having four separate electrically conductive discharge wires or coils 76, 78, 80, and 82 wound around and extending the length of distal portion 70 of the catheter. Conductors 75, 77, 79, and 81 connect conductive wires 76, 78, 80 and 82, respectively, to the defibrillator unit 25. Alternatively, the discharge wires may extend the length of the catheter and connect to the defibrillator unit without the need of conductors 75, 77, 79, and 81. The conductive wires are wound so that spaces are provided between adjacent wires along the length of the catheter 74. Insulation 83 is provided along the surface of distal portion 70 to insulate the conductive discharge wires from one another.

In use, electrode 72 is implanted in the vena cava region of the heart, and is energized by a pulse block such as that illustrated in FIG. 5a at 30, and achieves the advantages described above by the gatling discharge technique.

Figure 10:
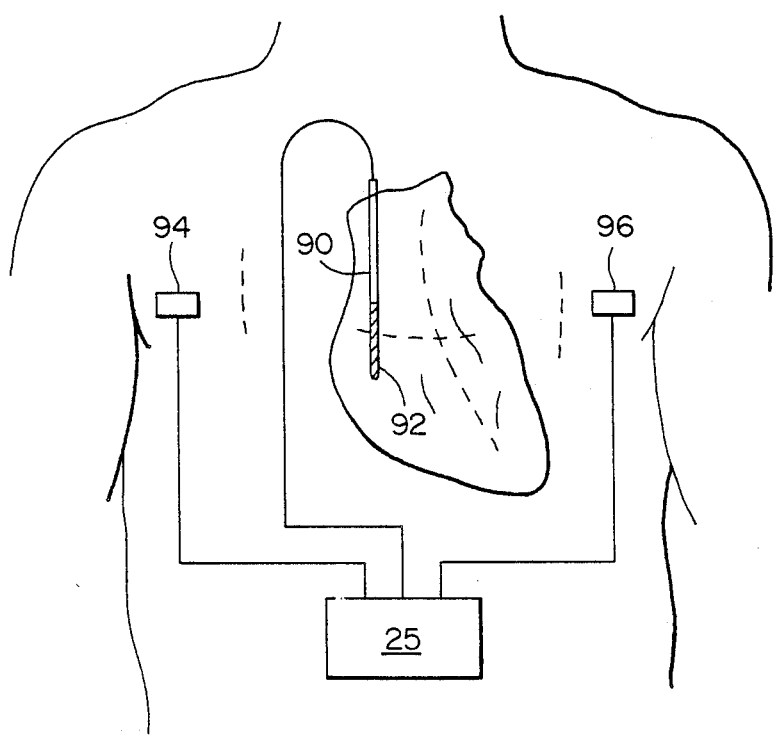
FIG. 10 is a schematic diagram illustrating the gatling discharge technique used in a multiple lead arrangement.

The specific types of waveform, or waveform shape, is not a necessary feature of the present invention. It is envisioned that any type of waveform or pulse block can be employed, just so long as it is segmented to effect the gatling discharge described hereinabove. Specifically, a pulse block of any shape can be timesampled to derive discrete pulse segments to be delivered to discrete conductive segments on an electrode. Furthermore, as illustrated in FIG. 10, the gatling discharge technique of the present invention can be applied to a multiple lead arrangement. Specifically, separate electrodes can be implanted about the heart to receive discrete pulse segments for changing the shock vector applied to the heart. One configuration may include a catheter 90 having a distal electrode 92 and implanted within the right ventricle. In addition, two subcutaneous patch electrodes 94 and 96 are provided, one being implanted over the sternum and one being implanted under the left arm.

In this configuration, a defibrillation pulse is segmented into three discrete segments and conveyed to the electrodes 92, 94, and 96 to effect gatling discharge between the electrodes. Typically, in this multi-electrode arrangement, the polarity of the pulse segments is kept the same to avoid affecting the voltage gradients of any particular muscle mass.

It should be understood that the above description is intended by way of example only and is not intended to limit the present invention in any way except as set forth in the following claims.

What is claimed is:

1. A defibriliation system for treating arrhythmias of the human hear with at least two implantable defibrillation electrodes for placement on, about, or in the heart for generating an electric field in the heart, the system comprising:
- an implantable defibrillation electrode having a discharge surface region adapted for facing and stimulating the heart, said discharge surface region comprising a plurality and a predetermined number of discrete conductive segments;
- pulse generating means for generating a series of discrete electrical pulse segments for supplying electrical energy to said discharge surface region; and
- directing means for directing select ones of said discrete electrical pulse segments to a particular one or ones of said discrete conductive segments so that only said particular one or ones and less than all of said predetermined number of said discrete conductive segments receive electrical energy from said pulse generating means at any instant of time.

2. The defibrillation system of claim 1, wherein said discrete conductive segments comprise stacked layers of discrete conductive mesh screens.

3. The defibrillation system of claim 1, wherein said discrete conductive segments comprise electrically conductive wires wound around a cardiac catheter.

4. The defibrillation system of claim 1, and further comprising a conductor means for electrically connecting select ones of said conductive segments together.

5. The defibrillation system of claim 1, wherein said pulse generating means comprises means for generating a series of discrete pulse segments within a single pulse.

6. The defibrillation system of claim 1, wherein said discharge surface region is supported entirely by a single defibrillation electrode.

7. A defibrillation system for treating arrhythmias of the human heart with at least two implantable defibrillation electrodes for placement on, about, or in the heart for generating an electric field in the heart, the system comprising:
- an implantable defibrillation electrode having a discharge surface region adapted for facing and stimulating the heart, said discharge surface region comprising a plurality and a predetermined number of discrete conductive segments;
- pulse generating means for generating an electrical pulse block;
- chopping means for chopping said pulse block into discrete pulse segments; and
- directing means for directing select ones of said discrete pulse segments to a particular one or ones of said discrete conductive segments so that only said particular one or ones and less than all of said predetermined number of said discrete conductive segments receive electrical energy from said pulse generating means at any instant of time.

8. The defibrillation system of claim 7, wherein said discrete conductive segments comprise electrically conductive wires wound around a cardiac catheter.

9. The defibrillation system of claim 7, wherein said discrete conductive segments comprise stacked layers of discrete conductive mesh screens.

10. The defibrillation system of claim 7, and further including conductive means for electrically connecting together select ones of said discrete conductive segments.

11. A defibrillation system for treating arrhythmias of the human heart with at least two implantable defibrillation electrodes for placement on, about, or in the heart for generating an electric field in the heart, the system comprising:
- an implantable defibrillation electrode having a discharge surface region adapted for facing and stimulating the heart, said discharge surface region comprised of a plurality and a predetermined number of discrete conductive segments;
- insulation means positioned between said conductive segments for insulating said segments from one another;
- a defibrillator unit including a pulse generator for generating an electrical pulse block, means for chopping said pulse block into discrete pulse segments, and means for directing said discrete pulse segments to select ones of said output terminals; and
- lead means comprising a plurality of electrical conductors for electrically connecting select ones of said conductive segments on said discharge region of said electrode with said defibrillator unit for directing select ones of said discrete pulse segments to a particular one or ones of said discrete conductive segments so that only said particular one or ones and less than all of said predetermined number of said discrete conductive segments receive electrical energy from said pulse generator at any instant of time.

12. The defibrillation system of claim 11, wherein said means to direct said electrical pulses comprises a switching circuit.

13. The defibrillation system of claim 11, wherein said discrete conductive segments comprise stacked layers of discrete conductive mesh screens.

14. The defibrillation system of claim 11, wherein said discrete conductive segments comprise electrically conductive wires wound around a cardiac catheter.

15. A defibrillation system for treating arrhythmias of the human heart with at least two implantable defibrillation electrodes for placement on or about the heart for generating an electric field in the heart, the system comprising:
- at least one implantable defibrillation electrode having a discharge surface region adapted for facing and stimulating the heart, said discharge region comprised of a plurality and a predetermined number of discrete conductive segments, insulation means positioned between conductive segments for insulating said conductive segments from one another, said electrode further including conductor means for electrically connecting select ones of said discrete conductive segments together;
- a defibrillator unit including a pulse generator for generating an electrical pulse block, means for chopping said pulse block into discrete pulse segments, and means to direct said discrete pulse segments to select ones of said output terminals; and
- a lead having a plurality of electrical conductors for electrically connecting select ones of said conductive segments on said discharge region of said electrode with said defibrillator unit for directing select ones of said discrete pulse segments to a particular one or ones of said discrete conductive segments so that only said particular one or ones and less than all of said predetermined number of said discrete conductive segments receive electrical energy from said pulse generator at any instant of time.

16. The defibrillation system of claim 15, wherein said means to direct said electrical pulses comprises a switching circuit.

17. The electrode of claim 15, wherein said discrete conductive segments comprise electrically conductive wires wound around the length of a catheter.

18. An implantable defibrillation electrode adapted for attachment to the human heart for applying electrical energy to said heart in conjunction with at least one another implantable electrode, said electrode being connected to a pulse generator means for producing a series of discrete pulse segments, the electrode comprising:
   a discharge surface region for facing and stimulating the heart, said discharge region comprised of a plurality and a predetermined number of discrete conductive segments, an insulation element positioned on a back surface region of said electrode opposite said discharge surface region; and
   lead means for electrically connecting said electrode to said pulse generator so that a particular one or ones of said discrete conductive segments of said discharge region receive select ones of said discrete pulse segments for supplying electrical energy to said discharge surface region so that only said particular one or ones and less than all of said predetermined number of said discrete conductive segments receive electrical energy from said pulse generator at any instant of time.

19. The implantable defibrillation electrode of claim 18, and further including insulator means positioned between said conductive segments for electrically isolating said conductive segments.

20. The electrode of claim 18, wherein said discrete conductive segments comprise stacked layers of discrete conductive mesh screens.

21. The electrode of claim 18, wherein said discrete conductive segments comprise electrically conductive wires wound around a cardiac catheter.

22. The electrode of claim 18, and further comprising conductor means for electrically connecting together select ones of said discrete conductive segments.

23. The electrode of claim 18, wherein said lead means comprises a plurality of electrical conductors, and said pulse generator means further includes a plurality of output terminals for receiving select ones of said discrete pulse segments, and wherein said plurality of electrical conductors electrically connect select ones of said discrete conductive segments with select ones of said output terminals.

24. The implantable defibrillation electrode of claim 18, wherein said discharge surface region is supported entirely by a single defibrillation electrode.

25. A method for stimulating the human heart experiencing an arrhythmia by applying electrical energy to the heart via at least two electrodes implanted on or about said heart, at least one of said electrodes comprising a discharge surface region having a plurality of discrete electrically conductive segments, said electrode being electrically connected to a pulse generator, said pulse generator producing a series of discrete electrical pulse segments which together define a total desired amount of electrical energy, the method comprising the steps of:
   (a) applying a discrete electrical pulse segment to a first discrete conductive segment of said electrode at a first instant of time;
   (b) applying a discrete electrical pulse segment to a second discrete conductive segment on said electrode at a second instant of time subsequent to said first intent of time; and
   (c) repeating steps (a) and (b) a predetermined number of times so that only one discrete conductive segment is energized at any instant of time and until the total desired amount of electrical energy is delivered to the heart.

26. A method for stimulating the human heart experiencing an arrhythmia by applying electrical energy to the heart via at least two electrodes implanted or or in the region of the heart, a first electrode comprising a discharge surface region having a plurality and a predetermined number of discrete electrically conductive segments for stimulating said heart, conductor elements for connecting together select ones of said conductive segments into first and second discrete groups, said electrode being electrically connected to a pulse generator, said pulse generator producing a series of discrete electrical pulse segments which together define a total desired amount of electrical energy, the method comprising the steps of:
   (a) applying a discrete electrical pulse segment to said first group of discrete conductive segments on said first electrode at a first instant of time;
   (b) applying a discrete electrical pulse segment to said second group of discrete conductive segments on said first electrode at a second instant of time subsequent to said first instant; and
   (c) repeating (a) and (b) a predetermined number of times so that only a single group and less than all of said predetermined number of discrete conductive segments is energized at any instant of time and until the total desired amount of electrical energy is delivered to the heart.

27. A method for stimulating the human heart experiencing an arrhythmia by applying electrical energy to the heart via at least two electrodes implanted on or in the region of the heart, a first electrode comprising a discharge surface region having a plurality and a predetermined number of discrete conductive segments for stimulating the heart, the method comprising the steps of:
   producing a series of discrete pulse segments; and
   directing select ones of said discrete pulse segments to a particular one or ones of said discrete conductive segments so that only said particular one or ones and less than all of said predetermined number of said discrete conductive segments are energized at any instant of time.

28. A method for stimulating the human heart experiencing an arrhythmia by applying electrical energy to the heart via at least two electrodes implanted on or in the region of the heart, a first electrode comprising a discharge surface region having a plurality and a predetermined number of discrete conductive segments for stimulating the heart, the method comprising the steps of:
   generating a pulse block;
   chopping said pulse block into a series of discrete pulse segments; and
   directing select ones of said discrete pulse segments to a particular one or ones of said discrete conductive segments so that only said particular one or ones and less than all of said predetermined number of said discrete conductive segments are energized at any instant of time until said pulse block is exhausted.

29. An implantable defibrillation electrode for attachment to the human heart for applying electrical energy to said heart in conjunction with at least one other implantable electrode, said electrode for being connected to a pulse generator producing a series of discrete pulse segments, said pulse segments being conducted to select ones of a plurality of output terminals of said pulse generator, the electrode comprising:
   a discharge surface comprised of a plurality of conductive mesh screens alternately stacked;
   a non-conductive mask element extending over substantially the entire discharge surface and having apertures for exposing said conductive mesh screens on the discharge surface;
   an insulation element positioned on the surface opposite said discharge surface region; and
   a lead having a plurality of electrical conductors for connecting select ones of said output terminals of said pulse generator with select ones of said conductive mesh screens.

30. A defibrillation system for treating arrhythmias of the human heart with at least two implantable defibrillation electrodes for placement on, about, or in the heart for generating an electric field in the heart, the system comprising:
   an implantable defibrillation electrode having a discharge surface region adapted for facing and stimulating the heart, said discharge surface region comprising a plurality and a predetermined number of discrete conductive segments;
   capacity means for storing and discharging electrical energy;
   capacitor charging means for charging said capacitor means to a predetermined voltage;
   a plurality of output terminals connected to select ones of said discrete conductive segments of said electrode;
   a plurality of switching means, each of said switching means being electrically connected to a first terminal of said capacitor means and capable of being electrically connected to a select one of said output terminals; and
   timing generator means connected to said plurality of switching means for generating a triggering sequence signal to trigger select ones of said plurality of switching means to connect a particular one or ones of said discrete conductive segments to said capacitor means for discrete predetermined time intervals as said capacitor means discharges for conveying select ones of said discrete pulse segments to said particular one or ones of said discrete conductive segments so that only said particular one or ones and less than all of said predetermined number of said discrete conductive segments are energized at any instant of time.

31. The system of claim 30, and further comprising a plurality of polarity switching means, each being connected to a second terminal of said capacitor means and to said timing generator means, and connected between each of said switching means and said output terminals, said polarity switching means being controlled by a polarity sequence signal produced by said timing generator means concurrently with said triggering sequence signal for reversing the polarity of said discrete pulse segments conveyed to said discrete conductive segments.

32. A defrillation system for treating arrhythmias of the human heart with at least two implantable defibrillation electrodes for placement on, about, or in the heart for generating an electric field in the heart, the system comprising:
   an implantable defibrillation electrode having a discharge surface region adapted for facing and stimulating the heart, said discharge surface region comprising a plurality and a predetermined amount of discrete conductive segments;
   generating means for generating electrical energy in the form of a defibrillation waveform; and
   directing means for directing said electrical energy to select one or ones of said discrete conductive segments so that only said select one or ones and less than all of said predetermined number of said discrete conductive segments are energized at any instant of time.

33. An implantable defibrillation electrode adapted for attachment to the human heart for applying electrical energy to said heart in conjunction with at least one other implantable electrode, said electrode being connected to a pulse generator means for producing electrical energy in the form of a defibrillation waveform, the electrode comprising:
   a discharge surface region for facing and stimulating the heart, said discharge surface region comprised of a plurality and a predetermined number of discrete conductive segments, an insulation element positioned on a back surface region of said electrode opposite said discharge surface region; and
   lead means for electrically connecting said electrode to said pulse generator means for directing said electrical energy to select one or ones of said discrete conductive segments so that only said select one or ones and less than all of said predetermined number of said discrete conductive segments are energized at any instant of time.

34. A gatling discharge defibrillation system for treating arrhythmias of the human heart with at least two implantable defibrillation electrodes for placement on, about, or in the heart for generating an electric field in the heart, the system comprising:
   an implantable defibrillation electrode having a discharge surface region adapted for facing and stimulating the heart, said discharge surface region comprising a plurality and a predetermined number of discrete conductive segments;
   pulse generating means for generating a series of discrete pulse segments; and
   directing means for directing select ones of said discrete pulse segments to a particular one or ones of said discrete conductive segments so that only said particular one or ones and less than all of said predetermined number of discrete conductive segments are energized at any instant of time for confining insulative gas produced as a result of the conversion of electric current to ionic current at an interface of said discharge surface region and the heart to each of said particular one or ones of said discrete conductive segments during each of said pulse segments, thereby lowering the amount of insulative gas across the entire discharge surface region to facilitate the conversion of electric current to ionic current across said discharge surface region.

35. A method for performing gatling discharge defibrillation of a fibrillating heart comprising the steps of:

placing at least two defibrilation electrodes on or about the heart;

producing a series of discrete electrical pulse segments which together define a total desired amount of electrical energy;

segmenting at least one of said defibrillation electrodes to define a discharge surface region comprised of a plurality and a predetermined number of discrete conductive segments; and directing select ones of said discrete electrical pulse segments to a particular one or ones of said discrete conductive segments so that only said particular one or ones and less than all of said predetermined number of said discrete conductive segments are energized at any instant of time.

36. A method for performing gatling discharge defibrillation of a fibrillating heart comprising the steps of:

placing at least two defibrillation electrodes on or about the heart;

segmenting at least one of said defibrillation electrodes to define a discharge surface region comprised of a plurality and a predetermined number of discrete conductive segments;

producing an electrical pulse block of a predetermined duration;

chopping said electrical pulse block into a plurality of discrete electrical pulse segments; and directing select ones of said discrete electrical pulse segments to a particular one or ones of said discrete conductive segments so that only said particular one or ones and less than all of said predetermined number of said discrete conductive segments is energized at any instant of time until said electrical pulse block is exhausted.

37. A defibrillation system for treating arrhythmias of the human heart with at least two implantable defibrillation electrodes for placement on, about, or in the heart for generating an electric field in the heart, the system comprising:

an implantable defibrillation electrode having a discharge surface region adapted for facing and stimulating the heart, said discharge surface region comprising a plurality of discrete conductive segments in the form stacked layers of discrete conductive mesh screens;

pulse generating means for generating a series of discrete electrical pulse segments for supplying electrical energy to said discharge surface region; and directing means for directing select ones of said discrete electrical pulse segments to select ones of said discrete conductive segments.

38. A defibrillation system for treating arrhythmias of the human heart with at least two implantable defibrillation electrodes for placement on, about, or in the heart for generating an electric field in the heart, the system comprising:

an implantable defibrillation electrode having a discharge surface region adapted for facing and stimulating the heart, said discharge surface region comprising a plurality of discrete conductive segments in the form of stacked layers of discrete conductive mesh screens;

a pulse generating means for generating an electrical pulse block;

chopping means for chopping said pulse block into discrete pulse segments; and directing means for directing select ones of said discrete pulse segments to select ones of said discrete conductive segments.

39. A defibrillation system for treating arrhythmias of the human heart with at least two implantable defibrillation electrodes for placement on, about, or in the heart for generating an electric field in the heart, the system comprising:

an implantable defibrillation electrode having a discharge surface region adapted for facing and stimulating the heart, said discharge surface region comprised of a plurality of discrete conductive segments in the form of stacked layers of discrete conductive mesh screens;

insulating means positioned between said conductive segments for insulating said segments from one another;

a defibrillator unit including a pulse generator for generating an electrical pulse block, means for chopping said pulse block into discrete pulse segments, and means for directing said and lead means comprising a plurality of electrical conductors for electrically connecting select ones of said conductive segments on said discharge region of said electrode with said defibrillator unit for directing select ones of said discrete pulse segments to a select ones of said discrete conductive segments.

40. An implantable defibrillation electrode adapted for attachment to the human heart for applying electrical energy to said heart in conjunction with at least one other implantable electrode, said electrode being connected to a pulse generator means for producing a series of discrete pulse segments, the electrode comprising:

a discharge surface region for facing and stimulating the heart, said discharge region comprised of a plurality of discrete conductive segments in the form of stacked layers of discrete conductive mesh screens, and insulation element positioned on a back surface region of said electrode opposite said discharge surface region; and lead means for electrically connecting said electrode to said pulse generator for directing select ones of said discrete conductive segments of said discharge region to select ones of said discrete pulse segments for supplying electrical energy to said discharge surface region.

41. A defibrillation system for treating arrhythmias of the human heart with at least two implantable defibrillation electrodes for placement on, about, or in the heart for generating an electric field in the heart, the system comprising:

an implantable defibrillation electrode having a discharge surface region adapted for facing and stimulating the heart, said discharge surface region comprising a plurality of discrete conductive segments;

generating means for generating electrical energy in the form of a defibrillation waveform; and directing means for directing said electrical energy to select one or ones of said discrete conductive segments so that only a portion of said discharge surface region is energized at any instant of time.

* * * * *

UNITED STATES PATENT AND TRADEMARK OFFICE
CERTIFICATE OF CORRECTION

PATENT NO. : 4,969,463

DATED : November 13, 1990

INVENTOR(S) : DAHL et al.

It is certified that error appears in the above-identified patent and that said Letters Patent is hereby corrected as shown below:

```
Column 1, line 35, delete "at" and insert --an--; and
         line 49, please delete "as can be reduced.  As
                  a result, the size".
Column 2, line 43, delete "5a" and insert --5--;
         lines 45-46, delete "invention.  FIG. 5b is a
                  plot of" and insert --invention, also
                  illustrating--; and
         lines 47-48, delete "pulse shown in FIG. 5a."
                  and insert --pulse.--.
Column 4, line 20, delete "C,," and insert --C',--;
         line 49, delete "5b" and insert --5--;
         line 56, delete "2, 5a, and 5b," and insert
                  --2 and 5,--; and
         line 64, delete "5b" and insert --5--.
Column 5, line 9, delete "5a" and insert --5--;
         line 13, delete "5b" and insert --5--; and
         line 46, delete "5a" and insert --5--.
Column 6, line 32, delete "5a" and insert --5--; and
         line 40, delete "timesampled" and insert
                  --time-sampled--; and
         line 67, delete "hear" and insert --heart--.
```

UNITED STATES PATENT AND TRADEMARK OFFICE
CERTIFICATE OF CORRECTION

PATENT NO. : 4,969,463

DATED : November 13, 1990

INVENTOR(S) : DAHL et al.

It is certified that error appears in the above-identified patent and that said Letters Patent is hereby corrected as shown below:

Title Page:
IN THE ABSTRACT

Line 13, delete "reduces" and insert --reduced--.

Signed and Sealed this

Twentieth Day of October, 1992

*Attest:*

DOUGLAS B. COMER

*Attesting Officer* — Acting Commissioner of Patents and Trademarks